United States Patent
Fautz

(10) Patent No.: US 9,095,272 B2
(45) Date of Patent: Aug. 4, 2015

(54) VESSEL-DEPENDENT FLIP ANGLE MODULATION IN TOF MR ANGIOGRAPHY

(75) Inventor: Hans-Peter Fautz, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 1275 days.

(21) Appl. No.: 12/629,485

(22) Filed: Dec. 2, 2009

(65) Prior Publication Data

US 2010/0145181 A1 Jun. 10, 2010

(30) Foreign Application Priority Data

Dec. 2, 2008 (DE) .......................... 10 2008 060 048

(51) Int. Cl.
| | | |
|---|---|---|
| A61B 5/05 | (2006.01) | |
| A61B 5/055 | (2006.01) | |
| A61B 5/02 | (2006.01) | |
| G01R 33/563 | (2006.01) | |
| G01R 33/483 | (2006.01) | |
| G01R 33/56 | (2006.01) | |

(52) U.S. Cl.
CPC ............. *A61B 5/055* (2013.01); *A61B 5/02007* (2013.01); *G01R 33/5635* (2013.01); *G01R 33/4835* (2013.01); *G01R 33/5601* (2013.01)

(58) Field of Classification Search
USPC .................................. 600/407, 410, 411, 419
See application file for complete search history.

(56) References Cited

U.S. PATENT DOCUMENTS

| | | | | |
|---|---|---|---|---|
| 5,337,749 A | * | 8/1994 | Shimizu ........................ | 600/419 |
| 6,842,638 B1 | * | 1/2005 | Suri et al. ..................... | 600/425 |
| 2003/0160611 A1 | * | 8/2003 | Miyoshi et al. ............... | 324/306 |
| 2007/0225588 A1 | * | 9/2007 | Steckner ....................... | 600/407 |
| 2008/0146951 A1 | * | 6/2008 | Zhao et al. .................... | 600/504 |

OTHER PUBLICATIONS

"Transmit SENSE," Katscher et al, Magnetic Resonance in Medicine, vol. 49 (2003), pp. 144-150.
"Parallel Excitation With an Array of Transmit Coils," Zhu, Magnetic Resonance in Medicine, vol. 51 (2004), pp. 775-784.
"A k-Space Analysis of Small-Tip-Angle Excitation," Pauly et al, Journal of Magnetic Resonance, vol. 81 (1989) pp. 43-56.
"Two-Dimensional Spatially Selective Spin Inversion and Spin-Echo Refocusing with a Single Nuclear Magnetic Resonance Pulse," Bottomley et al, Journal of Applied Physics, vol. 62, No. 10 (1987) pp. 4284-4290.
"PROGRESS in Efficient Three-Dimensional Spatially Localized in Vivo[31] PNMR Spectroscopy Using Multidimensional Spatially Selective (ρ) Pulses," Bottomley et al, Journal of Magnetic Resonance, vol. 74 (1987) pp. 550-556.
"Off-Axis Spatial Localization with Frequency Modulated Nuclear Magnetic Resonance Rotating (ρ) Pulses," Hardy et al, Journal of Applied Physics, vol. 63, No. 9 (1988) pp. 4741-4743.
"Improved MR Angiography: Magnetization Transfer Suppression with Variable Flip Angle Excitation and Increased Resolution," Atkinson et al, Radiology (1994) pp. 890-894.

* cited by examiner

*Primary Examiner* — Unsu Jung
*Assistant Examiner* — Shahdeep Mohammed
(74) *Attorney, Agent, or Firm* — Schiff Hardin LLP

(57) ABSTRACT

In a method to excite a magnetization in the generation of MR angiography images with the TOF technique, a slice plane is determined in which the magnetization for the generation of the MR angiography images should be excited, a position of a vessel in the slice plane is determined, and the magnetization is excited in the slice plane such that the magnetization in the vessel has a flip angle gradient in the direction of the vessel.

10 Claims, 2 Drawing Sheets

VESSEL-DEPENDENT FLIP ANGLE MODULATION IN TOF MR ANGIOGRAPHY

BACKGROUND OF THE INVENTION

1. Field of the Invention

The present invention concerns a method for excitation of a magnetization in the generation of MR angiography images with the TOF (time-of-flight) technique, and an MR system for implementing such a method.

2. Description of the Prior Art

Time-of-flight magnetic resonance angiography (TOF MR angiography) is a non-invasive imaging method for depiction of the vessel structure of an examination subject. It is based on the inflow of "fresh" spins, which have not been pre-saturated, into an imaging plane or, respectively, into an imaging volume. The stationary magnetization, i.e. the stationary spins of the imaging plane, is saturated by the repeated excitation in a short time interval TR. The signal of this magnetization is largely suppressed while the magnetization that has not been pre-saturated (which results via the blood flow into the imaging plan during the acquisition, for example) exhibits a high signal proportion.

The advantage of TOF MR angiography compared to contrast agent-intensified MR angiography is that it is not invasive, i.e. it does not use a contrast agent. Although contrast agent-intensified angiography methods have a wide range of use, contrast agents are not permitted for angiography in all countries. Furthermore, contrast agent-intensified angiography imaging methods should not be used for examination subjects with renal insufficiency.

TOF MR angiography has the disadvantage that the contrast between vessels and stationary tissue depends on the penetration depth of the unsaturated magnetization in the imaging plane. This means that the contrast is dependent on the blood flow speed and the orientation of the blood vessels to be depicted relative to the imaging plane. The best contrast is achieved when the vessel runs perpendicular to the imaging plane. As in stationary tissues, no unsaturated spins with high signal proportion can be resupplied into vessels that run parallel to the imaging plane, such that these vessels lose their contrast relative to the static environment within a certain vessel length. One possibility to minimize this contrast loss is to sequentially acquire only very thin individual slices so that the course of a vessel within an imaging plane is minimized. However, this individual slice method leads to a poor signal-to-noise ratio that can be achieved in a predetermined acquisition time. Furthermore, the achievable resolution perpendicular to the imaging plane is limited given the acquisition of individual slices.

In 3D acquisitions with volume excitation and two phase coding gradients, it is known to reduce the decreasing contrast in the flow direction in that a flip angle gradient perpendicular to the imaging plane is used, which leads to the situation that spins that have flowed further into the volume experience an increasing flip angle, and therefore contribute to more signal in order to reduce the decreasing magnetization in the vessels due to saturation effects (see D. Atkinson et al. in "Improved MR Angiography: Magnetization Transfer Suppression with Variable Flip Angle Excitation and Increased Resolution" in Radiology, 1994: Vol. 190, Pages 890-894).

The signal in the vessels remains thus can be made essentially constant across the volume, when the blood flow direction is perpendicular to the imaging plane. However, when the vessel does not run perpendicular to the imaging plane, the contrast of the vessels is reduced by saturation effects relative to the stationary environment, as mentioned above.

SUMMARY OF THE INVENTION

An object of the present invention is to show vessels that do not run perpendicular to the imaging plane in an improved manner in angiography imaging, using the time-of-flight technique.

According to a first aspect of the invention, a method is provided to excite the magnetization in the generation of MR angiography images with the time-of-flight technique. In one step of the method, a slice plane is determined in which the magnetization for the generation of the MR angiogram should be excited. Furthermore, the position of a vessel in the slice plane is determined and the magnetization in the slice plane is excited such that the magnetization in the vessel has a flip angle gradient in the direction of the vessel. According to the invention, a flip angle gradient is locally generated along an arbitrarily oriented vessel, wherein this gradient does not necessarily need to be perpendicular to the slice plane. For every vessel to be shown, a different flip angle gradient can be defined that follows this vessel.

For example, the flip angle gradient can be achieved in that RF pulses that are spatially selective are used simultaneously with magnetic field gradients. A spatial modulation of the generated transversal magnetization can be achieved via the switching of these pulses and the magnetic field gradients, wherein this spatial modulation is set depending on the position of the vessels. A target flip angle can be defined for every pixel or, respectively, for every voxel of the imaging volume. These target flip angles of the magnetization can be set so that a flip angle gradient results in every arbitrary vessel direction.

In order to achieve the spatial modulation of the transversal magnetization with a justifiable time cost, a system with multiple RF emitters that simultaneously emit RF pulses in order to achieve the flip angle gradients in the direction of the vessel with the switching of the magnetic field gradients is used to generate the RF pulses.

According to one embodiment of the invention, an examination region in the examination subject in which the slice plane lies from which the MR angiography images should be generated can be identified. The position of the vessel in the image plane can then be concluded with the identification of the examination region. For example, at least one anatomical feature in the examination subject can be identified that is compared with representative anatomical data whose vessel course path is known. The position of the vessel in the image plane can then be concluded via the comparison of the anatomical feature with the representative anatomical data. The identification of the position can hereby ensue independent of the examination subject, wherein this method is based on the fact that, if the examined body region or the examined body part is known, the preferred directions of the vessels in this body part are known.

In a further embodiment, the examination subject can be taken into account, wherein the variation of the anatomical feature relative to the representative anatomical data is taken into account from the comparison of the anatomical feature and the representative anatomical data, for example. Given the use of the method in the head, for example, the head shape of an examination subject can be compared with a representative head shape with known vessel structure. If the head of the examined person is larger or smaller or has a different shape, this variation can be taken into account in order to conclude the position of the vessel.

The invention furthermore pertains to an MR system to generate the MR angiography images with the TOF technique, wherein an acquisition unit with an RF unit is provided that excites the magnetization with radiation of RF pulses and is responsible for the switching of the magnetic field gradients. Furthermore, a slice determination unit is provided to determine a slice plane in which the magnetization should be excited. The MR system furthermore has a unit to determine the position of a vessel in the slice plane, wherein a control unit controls the excitation of the magnetization in the slice plane via the acquisition unit such that the magnetization in the slice plane in the vessel exhibits a flip angle gradient in the direction of the vessel. In order to be able to determine the position of the vessel in the slice plane, a unit to identify an examination region in the examination subject in which the slice plane lies can be provided, for example. A memory unit to store representative anatomical data is likewise provided. The unit to determine the position of the vessel can then identify the position of the vessels with the use of the identified examination region and with the use of the representative anatomical data.

As mentioned above, the RF unit is advantageously fashioned such that it has multiple RF emitters that can simultaneously emit RF pulses in the direction of the vessel to generate the flip angle gradient.

DESCRIPTION OF THE PREFERRED EMBODIMENTS

Figure 1:
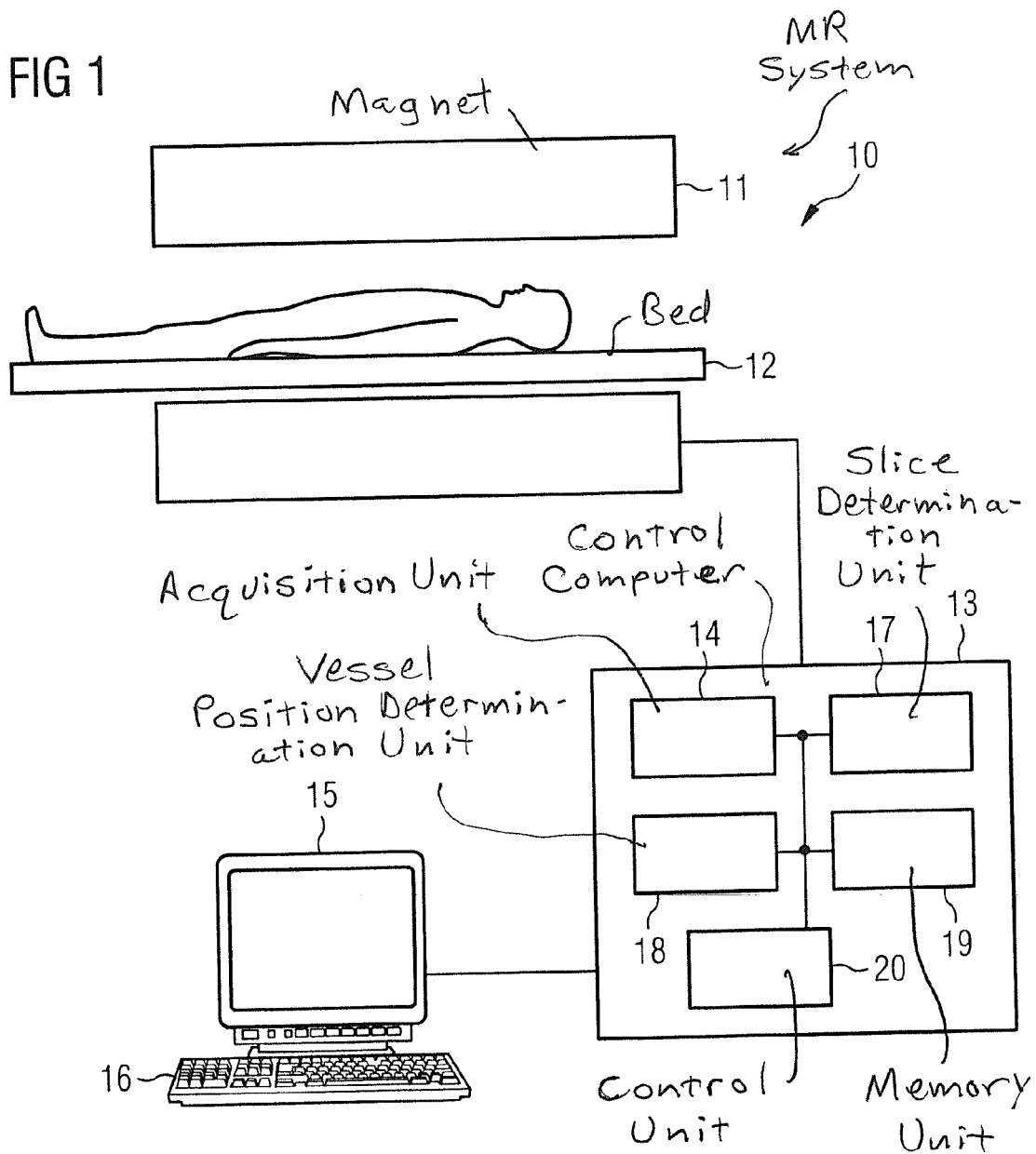
FIG. 1 shows an MR system with which a flip angle gradient in the direction of a vessel can be generated.

An MR system 10 that has a magnet 11 to generate a polarization field BO is shown in FIG. 1. An examination subject arranged on a bed 12 is driven into the isocenter of the magnet 11 in order to acquire MR images there. How MR images of the examination subject can be created via radiation of RF pulses and switching of magnetic field gradients is known to the man skilled in the art and is not explained in detail here. The MR system furthermore has a control computer 13 with which the MR system can be controlled. The control computer 13 has an acquisition unit 14 or image sequence control unit which has multiple RF emitter units to radiate simultaneous RF pulses. Furthermore, the acquisition unit 14 has a gradient controller to switch the temporally demarcated magnetic field gradients in connection with the RF pulses. An operator can acquire overview images of the examination subject 13 and display them on the monitor 15. The operator can then define the volume in which the TOF MR angiography measurement should be implemented, for example by positioning the volume on the overview images to be acquired. For example, an input unit 16 can be provided for this. A slice determination unit 17 determines the slice plane in which the magnetization for the generation of the MR angiography images should be excited, for example by localization of the volume that was set on the overview images relative to the MR system. Furthermore, a unit to determine the position of the vessels 18 in the individual slice planes is provided that determines the position of the vessels to be shown.

As will be explained in detail below, a memory unit 19 is provided for this purpose which, for example, stores representative anatomical data, and with whose help the unit 18 can determine the position of the vessels in the examination volume. A control unit 20 then controls the excitation of the magnetization in the acquisition unit 14 such that the magnetization in the slice plane in the vessel exhibits a flip angle gradient in the direction of said vessel.

The units shown in FIG. 1 are presented as functional units, but they can also be combined into other units. The division into units can likewise ensue differently than as shown, or it can be implemented as software in a processor.

Furthermore, a unit to identify the examination region is provided, which unit detects which anatomical region is acquired. This unit can be fashioned in the control unit 20, for example, and recognize—via segmentation of overview images in which the MR angiography measurement is planned—where in the body of the examination subject the angiography measurement should be conducted.

Figure 2:
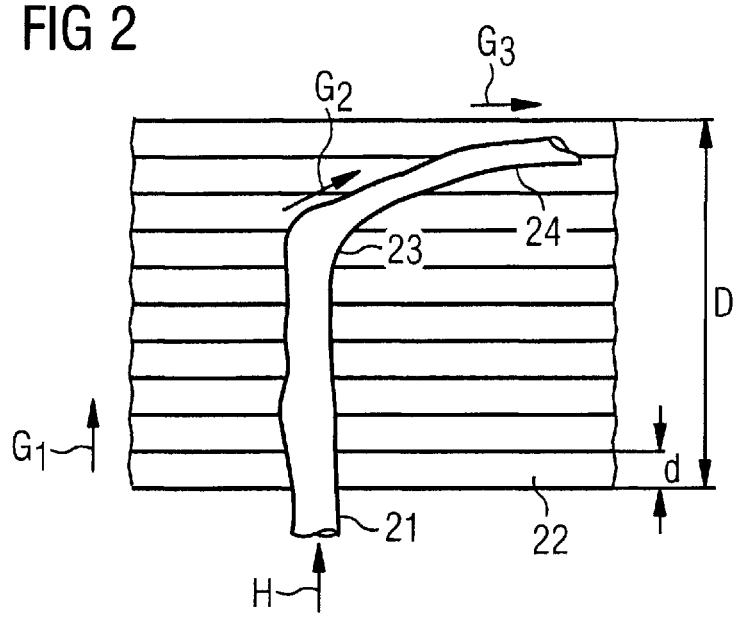
FIG. 2 shows an example of the position of a vessel with the different slice planes and the flip angle gradients to be generated.

The target volume D from which angiography exposures should be generated is schematically shown in FIG. 2. A blood vessel 21 through which blood flows in the flow direction F lies in the target volume. The target volume is acquired in multiple slice planes 22 that, for example, can have a thickness d.

In time-of-flight MR angiography, gradient echoes with short repetition times TR are acquired. By the repeated radiation of the RF pulses for the gradient echoes, the stationary tissue around the vessel 21 achieves a degree of saturation and delivers only a small signal contribution to the later MR angiography image. The spins flowing into the blood vessel 21 from outside the volume bring unsaturated spins into the volume, whereby the spins in the blood vessel possess a greater signal in the signal readout than the spins in the stationary tissue. In order to now prevent that the spin already contained in the target volume have less signal in the MR angiography image during their continuing flow, a magnetic field gradient perpendicular to the image or, respectively, slice plane in which the flip angle of the magnetization increases in the arrow direction $G_1$ can be introduced as is known from the prior art. However, in the event that the blood vessel 21 exhibits a greater proportion in the direction parallel to the slice plane, as shown in FIG. 2, the spins with flow components parallel to the slice plane have the same sat effect as the stationary spins outside of the vessel, whereby the signal intensity difference relative to the surrounding tissue decreases.

According to the present invention, the position of the vessel is now determined in every single slice plane, and therefore in the entire volume. For example, this can ensue in that the preferred direction of the vessels in the different body regions is essentially known. If the examined body region is now known, existing representative anatomical data that were produced in advance can be used in order to identify how the position in the vessel will be in the individual slice plane or, respectively, in the entire volume. For example, these representative anatomical data can exist in the form of an atlas in which the typical vessel structure for the different body regions is provided. The position of the examined volume or, respectively, of the individual slice planes can, for example, be determined with the aid of the overview exposures, wherein the anatomy of the examined subject (with which the representative vessel position can be determined from the atlas) can be detected via automatic or semi-automatic segmentation algorithms. In a preferred embodiment, the detected anatomy of the examination subject can be compared with the standard anatomy in the atlases, wherein then the representative position of the vessels known from the atlases can be adapted to the existing anatomy of the examination subject.

If the vessel course in the individual slice planes is now known, the RF system and the magnetic field gradients can then be controlled such that the flip angles of the magnetization have a gradient that follows the blood vessel course upon generation of the gradient echoes. In the example shown in FIG. 2, this would mean that—between the positions 23 and 24 where the blood vessel changes direction—the flip angle gradient is controlled so that the excited spins have a flip angle gradient in the direction of the vessel curve, as is schematically represented by the arrow $G_2$. An additional direction change occurs at position 24 of the vessel, such that the flip angle at these volume points in the vessel and around the vessel would have to be adjusted such that the flip angle gradient runs in the direction $G_3$.

Figure 3:
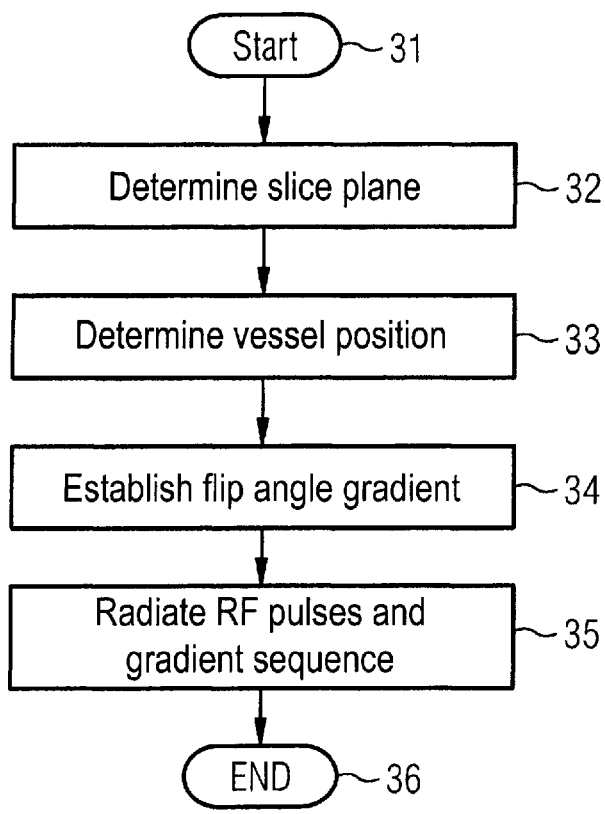
FIG. 3 is a flowchart of an embodiment of the method to generate a flip angle gradient in the direction of a vessel.

The steps that are implemented to generate the flip angle gradients depending on the vessel position are summarized in FIG. 3. After the start of the method in Step 31, the slice plane or, respectively, the slice planes in which the MR angiography data should be acquired is or, respectively, are defined in Step 32. The position of the vessel in the examined volume or the position of the vessels in the examined volume is subsequently determined in Step 33. As was mentioned in connection with FIG. 2, the determination of the position of the vessels can be established using anatomical features that have been determined in advance of the angiography measurement. Finally, the flip angle gradient for the different regions of the slice plane and of the entire volume can be determined in Step 34. The RF pulses and the magnetic field gradients are then radiated in Step 35 such that the flip angle gradients defined in Step 34 can be achieved upon magnetization. The TOF MR angiography can then be continued further (steps not shown) as is known from the prior art. The method to control the flip angle gradient ends in Step 36.

As is apparent from the above description, the optimal local gradient can be determined during the actual MR angiography measurement. It is possible to use different local flip angle gradients without it being necessary to acquire the entire MR angiography image.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to excite a magnetization for generation of time-of-flight (TOF) magnetic resonance (MR) angiography images, said method comprising the steps of:
   providing a computer with an electronic input that designates a target volume comprising multiple planar slices in an examination subject in which magnetization is to be excited for generation of TOF MR angiography images, said target volume containing a vessel that proceeds in respective vessel directions in the respective planar slices, said vessel directions being unknown in said computer at a time of said electronic input;
   in said computer executing a programmed algorithm in which a position of the vessel in each of said multiple planar slices is determined, and in which, from the respective positions, the vessel direction in which the vessel proceeds in each of said multiple planar slices is then determined, as a determined vessel direction; and
   from said computer, emitting control signals to a magnetic resonance system that operate a radio-frequency emitter and a gradient controller of the magnetic resonance system in coordination with each other to acquire MR signals from said target volume by exciting magnetization in said multiple planar slices to give magnetization in said vessel in each planar slice a flip angle gradient along the respective vessel direction of the vessel in the respective planar slice that is set, individually for each planar slice, dependent on the determined vessel direction of the vessel in the respective planar slice, so as to cause said MR signals to be of a substantially uniform signal strength throughout said target volume in said TOF MR angiography images.

2. A method as claimed in claim 1 comprising producing said flip angle gradient by, with said control signals simultaneous radiation of radio-frequency pulses by said radio-frequency emitter and activation of magnetic field gradients by said gradient controller.

3. A method as claimed in claim 1 comprising, in said programmed algorithm executed by said computer, determining the position of the vessel in the respective planar slices from the designated target volume.

4. A method as claimed in claim 1 comprising providing said computer with another electronic input that designates at least one anatomical feature in the examination subject and, in said programmed algorithm executed by said computer, comparing said at least one anatomical feature with representative anatomical data having a known vessel course therein, and determining said position of said vessel in said respective planar slices as a result of said comparison.

5. A method as claimed in claim 4 comprising, in said programmed algorithm executed by said computer, identifying anatomical variations of said examination subject with respect to said representative anatomical data, and implementing said comparison dependent on said anatomical variations.

6. A method as claimed in claim 1 comprising generating said flip angle gradient, with said control signals, by simultaneously radiating a plurality of radio-frequency pulses respectively from a plurality of radio-frequency emitters in said magnetic resonance system, with simultaneous activation of magnetic field gradients by said radio-frequency emitter.

7. A magnetic resonance system to excite a magnetization for generation of time-of-flight (TO F) magnetic resonance (MR) angiography images, comprising:
   an MR data acquisition unit comprising a radio-frequency emitter and a gradient controller;
   a computer having an input configured to receive an electronic entry that designates a target volume comprising slice planes in an examination subject in which magnetization is to be excited for generation of TOF MR angiography images, target volume containing a vessel that proceeds in respective vessel directions in the respective planar slices, said vessel directions being unknown in said computer at a time of said electronic input;
   said computer being configured to execute a programmed algorithm in which a position of the vessel in each of said multiple planar slices is determined, and in which, from the respective positions, the vessel direction in which the vessel proceeds in each of said multiple planar slices is then determined, as a determined vessel direction; and
   said computer being configured to emit control signals said MR data acquisition unit that operate said radio-frequency emitter and said gradient controller of the magnetic resonance system in coordination with each other to acquire MR signals from said target volume by exciting magnetization in said multiple planar slices to give magnetization in said vessel in each planar slice a flip angle gradient along the respective vessel direction of the vessel in the respective planar slice that is set, individually for each planar slice, dependent on the determined vessel direction of the vessel in the respective planar slice, so as to cause said MR signals to be of a substantially uniform signal strength said target volume in said TOF MR angiography images.

8. A magnetic resonance system as claimed in claim 7 wherein said computer is configured to receive another electronic input that designates at least one anatomical feature in the examination subject and, in said programmed algorithm executed by said computer, to compare said at least one anatomical feature with representative anatomical data having a known vessel course therein, and determine said position of said vessel in said multiple planar slices as a result of said comparison.

9. A magnetic resonance system as claimed in claim 7 wherein said computer is configured to emit said control signals to operate said MR data acquisition unit to produce said flip angle gradient by simultaneous radiation of radio-frequency pulses by said radio-frequency emitter and activation of magnetic field gradients by said gradient controller.

10. A magnetic resonance system as claimed in claim 9, wherein said MR data acquisition unit comprises a plurality of radio-frequency emitters, and wherein said computer is configured to emit said control signals to operate said MR data acquisition unit to generate said flip angle gradient by simultaneously radiating said plurality of radio-frequency pulses respectively from a plurality of radio-frequency emitters, with simultaneous activation of magnetic field gradients by said gradient controller.

* * * * *